United States Patent [19]

Dressler

[11] 4,108,907

[45] Aug. 22, 1978

[54] PROCESS FOR THE PREPARATION OF POLYALKYLBENZENE HYDROPEROXIDES

[75] Inventor: Hans Dressler, Monroeville, Pa.

[73] Assignee: Koppers Company, Inc., Pittsburgh, Pa.

[21] Appl. No.: 701,811

[22] Filed: Jul. 1, 1976

[51] Int. Cl.$^2$ ............................................ C07C 179/02
[52] U.S. Cl. ............................ 260/610 B; 260/610 A
[58] Field of Search ........................ 260/610 B, 610 A

[56] References Cited

U.S. PATENT DOCUMENTS 3,524,888  8/1970  Dressler et al. ................. 260/610 B

*Primary Examiner*—James O. Thomas, Jr.
*Assistant Examiner*—Werren B. Lone
*Attorney, Agent, or Firm*—Kenneth J. Stachel; Herbert J. Zeh, Jr.; Oscar B. Brumback

[57] ABSTRACT

Polyalkylbenzene hydroperoxides are prepared from a homogeneous solution at increased rates in the presence of sulfolane from polyalkylbenzenes which are poorly soluble or insoluble in sulfolane by preoxidizing the polyalkylbenzene to an oxidation level of at least 10 percent and less than 55 percent. Then the sulfolane is added and a homogeneous solution is formed and oxidation is continued to produce a hydroperoxide product at increased rates and to excellent conversions.

10 Claims, No Drawings

PROCESS FOR THE PREPARATION OF POLYALKYLBENZENE HYDROPEROXIDES

BACKGROUND OF THE INVENTION

This invention relates to a process for preparing hydroperoxides from polyalkylbenzenes in the presence of sulfolane.

The use of sulfolane to increase the rate of formation of hydroperoxides from alkyl- and polyalkylbenzenes is disclosed in U.S. Pat. No. 3,524,888. This patent also discloses that when an alkylbenzene like toluene, ethylbenzene, cumene or a polyalkylbenzene like orthoxylene, 1,3,5-trimethylbenzene or 4-isopropyl-o-xylene are oxidized in the presence of sulfolane a homogeneous solution is formed. The homogeneous solution enables better contact of the reactants and aids in the reaction and permits ready separation of the hydroperoxide products. When 5-isopropyl-m-xylene (3,5-dimethylcumene) was oxidized in the presence of sulfolane there was no apparent increase in the rate of formation of hydroperoxides. The lack of such an increase occurred because of the immiscibility of 5-isopropyl-m-xylene in sulfolane preventing the formation of a homogeneous reaction mixture.

It is well known to produce resorcinol or hydroquinone from meta-diisopropylbenzene or para-diisopropylbenzene, respectively, by oxidation to produce the dihydroperoxide which by cleavage with strong acid catalysts is converted to resorcinol or hydroquinone and acetone. The oxidation of both alkyl groups of the meta-, or para-diisopropylbenzene (DIPB) is readily inhibited and only partial oxidation can be achieved without considerable loss of efficiency and rate of oxidation. DIPB is oxidized first to the mono-hydroperoxide which is then further oxidized to the dihydroperoxide. In actual practice the reaction is stopped at a high mono-/dihydroperoxide ratio to reduce the formation of the numerous undesirable by-products otherwise formed in the oxidation of DIPB, such as carbinols, ketones, and carbinol-hydroperoxides which interfere with the oxidation. Increasing the temperature will increase the rate of reaction but it will also increase the formation of by-products. Therefore, a balanced operation requires relatively moderate temperatures of around 80°–90° C. Even at these conditions with a low rate of reaction the reaction eventually stops due to the inhibition of the oxidation by-products, and the ratio of DIPB-mono-/-dihydroperoxide is high.

It would be most desirable to increase the rate of reaction to hydroperoxides and to increase the conversion to DIPB-dihydroperoxide by oxidizing the DIPB in the presence of sulfolane. Unfortunately, the DIPB, as well as 5-isopropyl-m-xylene, and other polyalkylbenzenes, which have at least one alkyl group having three or more carbon atoms where one carbon atom is a tertiary carbon atom, including compounds such as 1,3,5-triisopropylbenzene, is immiscible with sulfolane. This immiscibility prevents the formation of a homogeneous reaction mixture and, therefore, also prevents the benefit of higher reaction rates in the production of hydroperoxides from the above-mentioned compounds.

It is an object of this invention to provide a process to enable the formation of a homogeneous reaction mixture when polyalkylbenzenes that are immiscible in sulfolane are oxidized in the presence of sulfolane to obtain an increased rate of reaction in the formation of hydroperoxides.

SUMMARY OF THE INVENTION

According to the process of this invention polyalkylbenzenes of the formula:

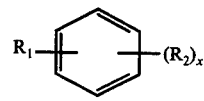

wherein $R_1$ is an alkyl group having 3–6 carbon atoms, one of which is a tertiary carbon, and $R_2$ is an alkyl group having 1 to 6 carbon atoms, the arrangement of which causes poor solubility in sulfolane and where $x$ is an integer from 1 to 3, can be oxidized in the presence of sulfolane to obtain an increase in the rate of formation of hydroperoxides. The process of this invention comprises contacting the polyalkylbenzene in the liquid phase and at a temperature in the range of 75° to 150° C. with oxygen to oxidize at least 10 percent of the polyalkylbenzene. Then sulfolane (tetrahydrothiophene dioxide) is added to form a homogeneous solution and the oxidation is continued to produce a product mixture containing hydroperoxides. The product mixture can then be contacted with water to separate the mixture into two phases. The phases are separated and the hydroperoxides recovered.

DETAILED DESCRIPTION OF THE INVENTION

Polyalkylbenzenes which are preoxidized by the process of this invention are those that are immiscible with sulfolane, for example, meta-diisopropylbenzene, para-diisoproylbenzene, 5-isopropyl-m-xylene, triisopropylbenzene and diisopropyl toluene. The polyalkylbenzenes become miscible with sulfolane after being treated by the preoxidation step of the present invention. The homogeneous solution, wherein sulfolane is the solvent, and which is formed as a result of this miscibility, provides many benefits. These benefits are illustrated in U.S. Pat. No. 3,524,888 which is hereby incorporated by reference. The predominant benefit is that the rate of formation of hydroperoxides from the polyalkylated aromatic hydrocarbon is increased. Generally, the process of the present invention does not vary depending on what polyalkylbenzene is used, but any minor variations are within the ability of one skilled in the art.

In the preferred embodiment of the present invention meta-diisopropylbenzene (m-DIPB) is used as the polyalkylbenzene since its dihydroperoxide can be cleaved by strong acid catalysts to produce resorcinol. Also, the hydroperoxide solution could be used for the production of a mixture of isopropylphenol and dihydric phenol by the acid-catalyzed cleavage of the mixed DIPB-mono-/dihydroperoxide. The m-DIPB is added in the liquid state to any suitable oxidation reactor to give good gas/liquid contact, which is capable of maintaining oxygen pressure at the desired level and which may be equipped with an agitation device. Gaseous oxygen or an oxygen containing gas, such as air, or oxygen in admixture with a non-reactive gas, such as nitrogen, is normally added near the bottom of the reactor to improve the contact between the oxygen and the liquid m-DIPB. The rate of oxygen flow can be varied over a wide range and such rates are known to those skilled in the art. The reaction is in the liquid phase at temperatures between 75°–150° C. Atmospheric pressure is preferable although superatmospheric pressures may be used. The reaction time is sufficient to allow at least about 10 percent and preferably 15 to 25 percent oxidation of the m-DIPB. Although any percent of oxidation of m-DIPB above about 10 percent may be used, a practical limit above which the invention is less beneficial and less economic is around 55 percent oxidation of m-DIPB. The higher amounts, around 55 percent, of oxidation of m-DIPB are useful when the m-DIPB contains impurities.

As in conventional hydroperoxide producing processes, the reaction is performed in the presence of small amounts of basic metal salts, oxides, or hydroxides. The amounts used should be that which is sufficient to neutralize acidic compounds formed during the reaction. The carbonates, hydroxides, and acetates of the alkali metals, and oxides or hydroxides of alkaline earth metals are preferred. Examples include magnesium oxide, sodium carbonate, sodium acetate and the like. In addition to basic metal salts, oxides, or hydroxides, a catalytic amount of an initiator such as diisopropylbenzene monohydroperoxide is added to the reaction.

After the desired level of oxidation has been achieved the sulfolane is added to the reaction mixture. The amount of sulfolane added is between 25 to 150 percent based on the weight of m-DIPB. Lesser amounts do not give the four-fold or more increase in the rate of hydroperoxide formations while the use of more than about 150 percent does not provide any additional benefits and would be uneconomical. After the addition of the sulfolane the reaction mixture is a homogeneous mixture. The oxidation of this homogeneous mixture is continued at the same conditions of temperature and pressure as the pre-oxidation until optimum oxidation is achieved.

The amount of oxidation may be measured by periodic sampling of the reaction mixture and determining the amount of oxidized products of m-DIPB present in the reaction mixture. This determination may be performed by any method known to those skilled in the art.

The homogeneous solution of hydroperoxides in sulfolane also permits ready separation of the hydroperoxide. The addition of water to the homogeneous reaction mixture after the oxidation causes a phase separation. By this phase separation the bulk of the hydroperoxide is carried by the solvent into the water phase. Then merely by decantation or the like, the phases can be separated and the hydroperoxides concentrated or decomposed to useful products by conventional means. For example, the separated hydroperoxides can be decomposed by acid catalysis to make mono- and/or dihydric phenols and acetone. In addition the acid-catalyzed decomposition can be performed on the water-separated sulfolane phase rather than directly on the hydroperoxides.

The process can be operated as a batch process or can be carried out as a continuous operation. The oxidation reaction zones may consist of one or more than one vessel. One vessel may be used for the preoxidation reaction zone and another vessel may be used for the oxidation reaction zone. In the case of a continuous operation, the effluent from preoxidation may be cascaded from the preoxidation vessel to the oxidation vessel to which the sulfolane is added.

In order to better illustrate the operation of the process of the present invention the following examples are provided. These examples are for illustrative purposes and do not limit the broader process as previously described.

EXAMPLE 1

A stirred mixture of 100 grams of para-diisopropylbenzene (p-DIPB), 2.0 grams of sodium acetate and 1.0 grams of diisopropylbenzene (mono) hydroperoxide was aerated at 125° C. for 3.5 hours at which point the level of oxidation was 26.5 percent based on the hydroperoxide content calculated as mono-hydroperoxide. To this mixture 100 grams of sulfolane was added and the solution was further oxidized for 3.5 hours at 125° C. After this oxidation the total hydroperoxide content (based on the p-DIPB charged and calculated as DIPB-monohydroperoxide) was 74 wt. percent. The hydroperoxide product was anaylzed by nuclear magnetic resonance (NMR) spectroscopy and it was found that 65 percent of the p-DIPB was oxidized and the mole ratio of p-DIPB-mono-hydroperoxide/-dihydroperoxide was 2.4.

EXAMPLE 2

A stirred mixture of 100 grams of meta-diisopropylbenzene (m-DIPB), 2.0 grams of sodium acetate and 1.0 gram of diisopropylbenzene monohydroperoxide was aerated at 125° C. for 3.0 hours. At this point the level of oxidation was 19.4 percent based on the weight percent of hydroperoxide (calculated as monohydroperoxide). To this mixture 100 grams of sulfolane was added and the oxidation was continued for 7.0 hours at 125° C. The total hydroperoxide content based on the m-DIPB charged and calculated as DIPB-monohydroperoxide was 96 weight percent. The hydroperoxide product was analyzed by NMR spectroscopy and it was found that 80 percent of the m-DIPB was oxidized and the mole ratio of m-DIPB-mono-hydroperoxide/dihydroperoxide was 1.0. Also, it was found that only 5 percent of the starting material had been converted to undesirable by-products.

According to the provisions of the patent statutes the principle and preferred mode of operation of the invention have been illustrated and described. However, it should be understood that within the scope of the appended claims the invention may be practiced otherwise than as specifically illustrated and described.

I claim:

1. In a process for the hydroperoxidation of polyalkylbenzenes of the formula:

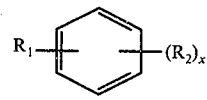

wherein $R_1$ is an alkyl group having three to six carbon atoms, one of which is a tertiary carbon; and $R_2$ is an alkyl group having one to six carbon atoms and $x$ is an integer from 1 to 3 and that have a poor solubility in sulfolane, which comprises contacting said polyalkylbenzene in the liquid phase with oxygen or an oxygen-containing gas mixture at a temperature of 75° to 150° C in the presence of sulfolane in an amount of 25 to 150 percent by weight based on the amount of said polyalkylbenzene, the improvement comprising:

(a) contacting said polyalkylbenzene in the liquid phase with oxygen to oxidize the polyalkylbenzene at least by about 10 percent based on the amount of polyalkylbenzene before the addition of the 25 to 150 percent by weight of sulfolane and the continuation of the oxidation in order to effect a homogeneous solution of said polyalkylbenzene and sulfolane at reaction conditions.

2. Process according to claim 1 wherein the polyalkylbenzene is contacted with oxygen to oxidize about 15 to about 25 percent of the polyalkylbenzene before the polyalkylbenzene is oxidized in the presence of sulfolane.

3. Process according to claim 1 wherein the alkylbenzene is selected from the group consisting of meta-diisopropylbenzene, para-diisopropylbenzene, triisopropylbenzene, diisopropyltoluene and 5-isopropyl-m-xylene.

4. Process according to claim 1 wherein the hydroperoxides produced are decomposed by acid catalysis to produce monohydric or dihydric phenols and acetone.

5. In a process for producing hydroperoxides from a polyalkylbenzene selected from the group consisting of 5-isopropyl-m-xylene, diisopropylbenzene, triisopropylbenzene, and diisopropyltoluene by contacting in the liquid phase with oxygen at a temperature of 75° to 150° C. in the presence of 25 to 150 weight percent of sulfolane based on the amount of the polyalkylbenzene to produce a product mixture containing the hydroperoxide, the improvement comprising:

contacting the alkylbenzene with oxygen at a temperature of 75° to 150° C in the liquid phase to oxidize at least about 10 percent of said hydrocarbon before the alkylbenzene is oxidized in the presence of the sulfolane to form a homogeneous reaction mixture.

6. Process according to claim 5 wherein the alkylbenzene is contacted with oxygen to oxidize about 15 to about 25 percent of the polyalkylbenzene before the polyalkylbenzene is oxidized in the presence of sulfolane.

7. Process according to claim 5 wherein the diisopropylbenzene is meta-diisopropylbenzene.

8. Process according to claim 5 wherein the diisopropylbenzene is para-diisopropylbenzene.

9. Process according to claim 5 wherein the hydroperoxides produced are decomposed by acid catalysis to monohydric or dihydric phenols and acetone.

10. A process for producing a hydroperoxide of a polyalkylbenzene selected from the group consisting of 5-isopropyl-m-xylene, meta- or para-diisopropylbenzene, triisopropylbenzene and diisopropyltoluene which comprises:

(a) contacting the polyalkylbenzene in the liquid phase with oxygen to oxidize about 15 to about 25 percent of the polyalkylbenzene;

(b) adding sulfolane in the amount of 25 to 150 percent by weight based on the amount of the polyalkylbenzene to form a mixture of partially oxidized polyalkylbenzene and sulfolane;

(c) contacting said mixture in the liquid phase with oxygen at a temperature of 75° to 150° C. to produce a mixture containing the hydroperoxide;

(d) adding water to said product mixture to separate the mixture into two phases; and (e) separating the phases and recovering the hydroperoxide therefrom.

* * * * *